United States Patent [19]

Sondermeyer et al.

[11] Patent Number: 5,081,022

[45] Date of Patent: Jan. 14, 1992

[54] VECTOR FOR THE CLONING AND EXPRESSION OF γ-INTERFERON, TRANSFORMED BACTERIA AND PROCESS FOR THE PREPARATION OF γ-INTERFERON

[75] Inventors: Paul Sondermeyer, Ostwald; Michael Courtney; Luc-Henri Tessier, both of Strasbourg; Jean-Pierre Lecocq, Rechsteet, all of France

[73] Assignee: Transgene S.A., Paris, France

[21] Appl. No.: 360,305

[22] Filed: Jun. 2, 1989

Related U.S. Application Data

[63] Continuation of Ser. No. 768,119, filed as PCT/FR84/00287, Dec. 5, 1984, abandoned.

[30] Foreign Application Priority Data

Dec. 9, 1983 [FR] France .................. 83 19777

[51] Int. Cl.$^5$ .................. C12N 15/70; C12N 15/11; C12N 15/00; C12P 21/02
[52] U.S. Cl. .................. 435/69.51; 435/252.3; 435/252.33; 435/320.1; 536/27; 935/6; 935/38; 935/45; 935/47; 935/73
[58] Field of Search .................. 435/69.51, 71.2, 91, 435/172.1, 172.3, 252.3–252.35, 849, 320; 536/27; 935/6, 9, 38, 45, 47, 73

[56] References Cited

U.S. PATENT DOCUMENTS 4,578,355  3/1986  Rosenberg .................. 435/172.3
4,582,800  4/1986  Crowl .................. 435/69.51
4,695,623  9/1987  Stabinsky .................. 530/351
4,762,791  8/1988  Goeddel et al. .................. 435/240.2

FOREIGN PATENT DOCUMENTS 0041767  12/1981  European Pat. Off. .......... 435/172.3

OTHER PUBLICATIONS

Gray et al; Nature 295: 503 (1982).
Gene, vol. 13, 1981, Elsevier/North-Holland Biomedical Press; A. Honigman et al: "Plasmid vectors for positive selection of DNA inserts controlled by the lambda rho L promoter, repressor and antitermination function", pp. 289–298.

*Primary Examiner*—James Martinell
*Attorney, Agent, or Firm*—Cushman, Darby & Cushman

[57] ABSTRACT

The present invention relates to a vector for the expression of the protein of human γinterferon in bacteria, of the type containing the gene which codes for the protein of human γinterferon and the plasmid elements which provide for the expression of this gene, wherein the 5' end of the sequence coding for the protein is as follows:

5' $\overline{ATG}$ TGC TAC TGT CAG GAT CCC 3'

TAC ACG ATG ACA GTC CTA GGG

Met  Cys  Tyr  Cys  Gln  Asp  Pro.

The bacteria transformed by these vectors enable γ-IFN to be produced in high yield.

14 Claims, 16 Drawing Sheets

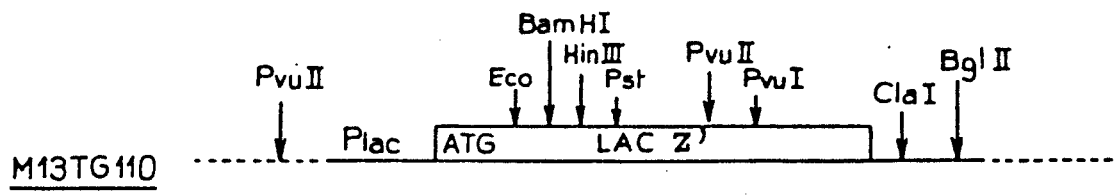
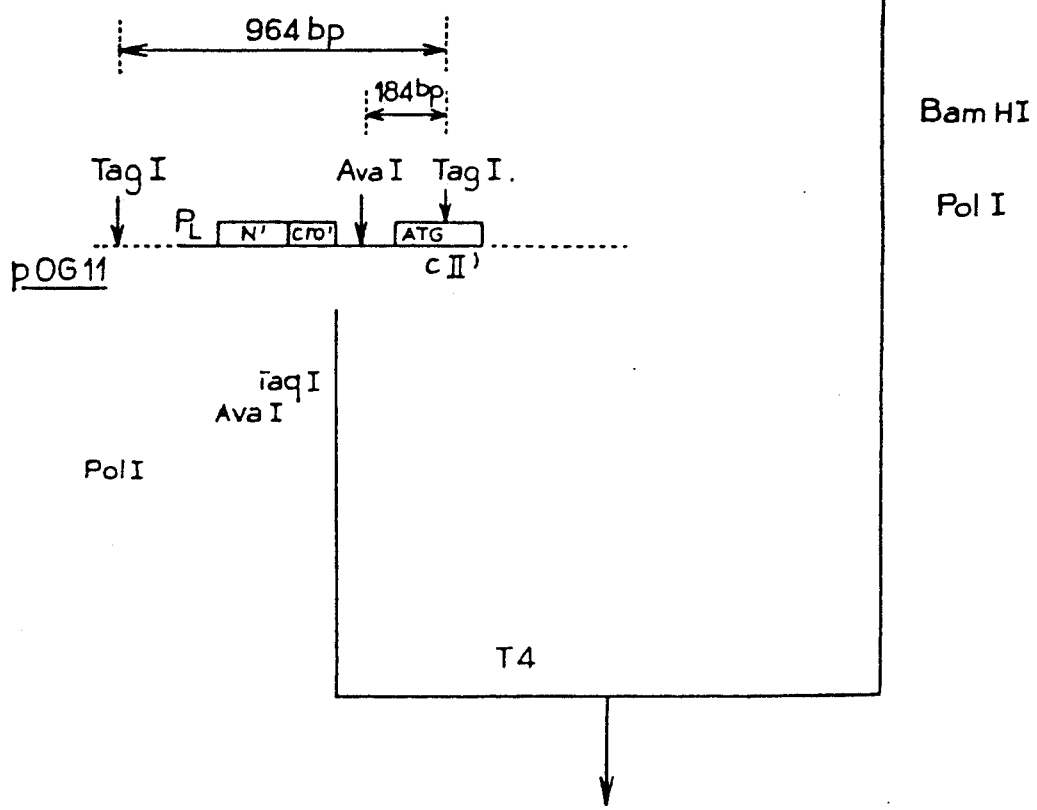
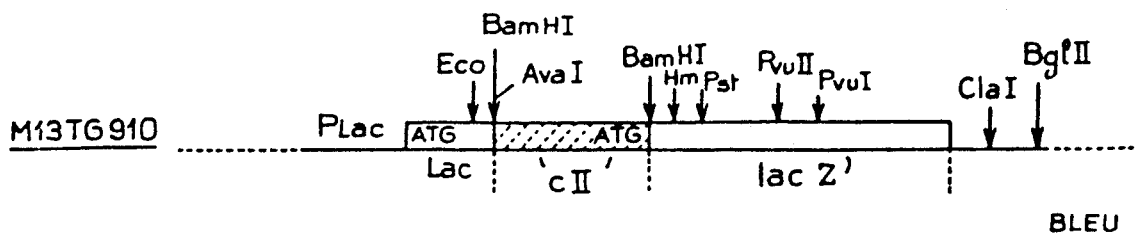
FIG_2

FIG. 3A.

```
          10         20         30         40         50         60
GATTTCGGAA CCACCATCAA ACAGGATTTT CGCCTGCTGG GGCAAACCAG CGTGGACCGC
CTAAAGCCTT GGTGGTAGTT TGTCCTAAAA GCGGACGACC CCGTTTGGTC GCACCTGGCG
         130        140        150        160     lacI 170        180
                         NarI/KasII
GTGAAAAGAA AAACCACCCT GGCGCCCAAT ACGCAAACCG CCTCTCCCCG CGCGTTGGCC
CACTTTTCTT TTTGGTGGGA CCGCGGGTTA TGCGTTTGGC GGAGAGGGGC GCGCAACCGG
         250        260        270        280        290        300
                         EcoRI     BamHI/AvaI
CGCAATTAAT GTGAGTTACC TCACTCATTA GGCACCCCAG GCTTTACACT TTATGCTTCC
GCGTTAATTA CACTCAATGG AGTGAGTAAT CCGTGGGGTC CGAAATGTGA AATACGAAGG
         370   EcoRI  380 BamHI/AvaI 390        400        410        420
CCATGATTAC GAATTCCCCG GATCCGAGT AACAAAAAAA CAACAGCATA AATAACCCG
GGTACTAATG CTTAAGGGGC CTAGGCTCA TTGTTTTTTT GTTGTCGTAT TTATTGGGC
         490        500  C1  520  Fmet CII  RBS 540
ATTTATTGC ATACATTCAA TCAATTGTTA TCTAAGGAA TACTTACATA TGGTTCGTGC
TAAATAACG TATGTAAGTT AGTTAACAAT AGATTCCTT ATGAATGTAT ACCAAGCACG
         610        620        630        640        650        660
ACTGGCCGTC GTTTTACAAC GTCGTGACTG GGAAAACCCT GGCGTTACCC AACTTAATCG
TGACCGGCAG CAAAATGTTG CAGCACTGAC CCTTTTGGGA CCGCAATGGG TTGAATTAGC
```

FIG.3C.

```
       730        740        750         HaeIII     770        780
CCCTTCCAA  CAGTTGCGTA  GCCTGAATGG  CGAATGGCGC  TTTGCCTGGT  TTCCGGCACC
GGGAAGGGTT  GTCAACGCAT  CGGACTTACC  GCTTACCGCG  AAACGGACCA  AAGGCCGTGG
                                              LAC Z'
       850        860        870        880        890        900
CCCCTCAAAC  TGGCAGATGC  ACGGTTACGA  TGCGCCCATC  TACACCAACG  TAACCTATCC
GGGGAGTTTG  ACCGTCTACG  TGCCAATGCT  ACGCGGGTAG  ATGTGGTTGC  ATTGGATAGG 970        980        990        1000       1010       1020
ATTTAATGTT  GATGAAAGCT  GGCTACAGGA  AGGCCAGAGC  CGAATTATTT  TTGATGGCGT
TAAATTACAA  CTACTTTCGA  CCGATGTCCT  TCCGGTCTGC  GCTTAATAAA  AACTACCGCA 1090       1100       1110       1120       1130       1140
TTAACGTTTA  CAATTTAAAT  ATTTGCTTAT  ACAATCTTCC  TGTTTTTGGG  GCTTTTTCTGA
AATTGCAAAT  GTTAAATTTA  TAAACGAATA  TGTTAGAAGG  ACAAAAACCC  CGAAAAGACT
                                                        BglII
       1210       1220       1230       1240       1250       1260
CTTGTTTGCT  CCAGACTCTC  AGGCAATGAC  CTGATAGCCT  TTGTAGATCT  CTCAAAAATA
GAACAAACGA  GGTCTGAGAG  TCCGTTACTG  GACTATCGGA  AACATCTAGA  GAGTTTTTAT
```

FIG. 3D.

```
          790       800       810       820       830       840
    AGAAGCGGGTG CCGGAAAGCT GGCTGGAGTG CGATCTTCCT GAGGCCGAGA CNGTCGTCGT
    TCTTCGCCAC  GGCCTTTCGA CCGACCTCAC GCTAGAAGGA CTCCGGCTGT GKCAGCAGCA 910       920       930       940       950       960
    CATTACGGTC AATCCGCCGT TTGTTCCCAC GGAGAATCCG ACGGGTTGTT ACTCGCTCAC
    GTAATGCCAG TTAGGCGGCA AACAAGGGTG CCTCTTAGGC TGCCCAACAA TGAGCGAGTG 1030      1040      1050      1060      1070      1080
    TCCTATTGGT TAAAAATGA  GCTGATTTAA CAAAAATTTA ACGGAATTT  TAACAAAATA
    AGGATAACCA ATTTTTACT  CGACTAAATT GTTTTTAAAT TGCGCTTAAA ATTGTTTTAT.

1150      1160      1170      1180      1190      Cla II 1200
    TTATCAACCG GGGTACATAT GATTGACATG CTAGTTTTAC GATTACCGTT CATCGATTCT
    AATAGTTGGC CCCATGTATA CTAACTGTAC GATCAAAATG CTAATGGCAA GTAGCTAAGA 1270      1280         3         13         23         33
    GCTACCCCTCT CCGGCATGAA TTTATCA
    CGATGGGAGA GGCCGTACTT AAATAGT
```

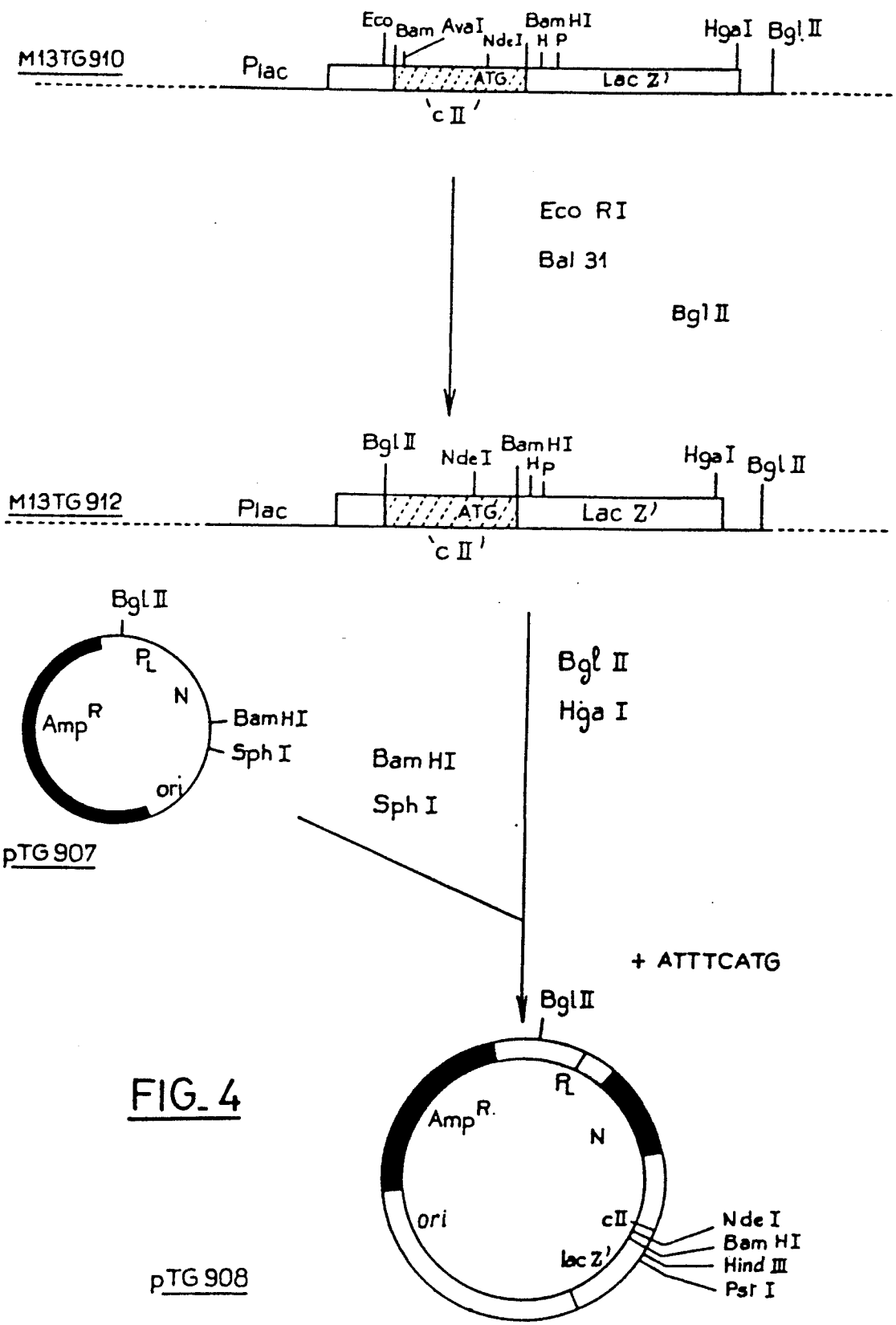
FIG._4

FIG.5A.

```
 43 ATG AAA TAT ACA AGT TAT ATC TTG GCT TTT CAG CTC TGC ATC
    Met Lys Tyr Thr Ser Tyr Ile Leu Ala Phe Gln Leu Cys Ile
                                          73

133 GCA GAA AAC CTT AAG AAA TAT TTT AAT GCA GGT CAT TCA GAT
    Ala Glu Asn Leu Lys Lys Tyr Phe Asn Ala Gly His Ser Asp
                                         163

223 GAG GAG AGT GAC AGA AAA ATA ATG CAG AGC CAA ATT GTC TCC
    Glu Glu Ser Asp Arg Lys Ile Met Gln Ser Gln Ile Val Ser
                                         253

313 AAG AGT GTG GAG ACC ATC AAG GAA GAC ATG AAT GTC AAG TTT
    Lys Ser Val Glu Thr Ile Lys Glu Asp Met Asn Val Lys Phe
                                         343

403 TAT TCG GTA ACT GAC TTG AAT GTC CAA CGC AAA GCA ATA CAT
    Tyr Ser Val Thr Asp Leu Asn Val Gln Arg Lys Ala Ile His
                                         433

493 AAG CGA AAA AGG AGT CAG ATG CTG TTT CAA GGT CGA AGA GCA
    Lys Arg Lys Arg Ser Gln Met Leu Phe Gln Gly Arg Arg Ala
                                         523
```

FIG.5B.

```
GGGGGGGGGGGAACTTCTTTGGCTTAATTCTCTCGGAAACG
                                        103
GTT TTG GGT TCT CTT GGC TGT TAC TGC CAG GAC CCA TAT GTA AAA GAA
Val Leu Gly Ser Leu Gly Cys Tyr Cys Gln Asp Pro Tyr Val Lys Glu
                                        193
GTA GCG GAT AAT GGA ACT CTT TTC TTA GGC ATT TTG AAG AAT TGG AAA
Val Ala Asp Asn Gly Thr Leu Phe Leu Gly Ile Leu Lys Asn Trp Lys
                                        283
TTT TAC TTC AAA CTT TTT AAA AAC TTT AAA GAT GAC CAG AGC ATC CAA
Phe Tyr Phe Lys Leu Phe Lys Asn Phe Lys Asp Asp Gln Ser Ile Gln
                                        373
TTC GAT AGC AAC AAA AAG CGA GAT GAC TTC GAA AAG CTG ACT AAT
Phe Asp Ser Asn Lys Lys Lys Arg Asp Asp Phe Glu Lys Leu Thr Asn
                                        463
GAA CTC ATC CAA GTG ATG GCT GAA CTG TCG CCA GCA GCT AAA ACA GGG
Glu Leu Ile Gln Val Met Ala Glu Leu Ser Pro Ala Ala Lys Thr Gly
                                        553
TCC CAG TAA TGG TTG TCC TGC CTG CAA TAT TTG AAT TTT AAA TCT AAA
Ser Gln ***
```

FIG. 5C.

```
583
TCTATTTATTAATATTAACATTATTTATGGGGAATATATTTTTAGACTCATCA
      613
703
TTATTTATAATTCCTATATCCTGTGACTGTCTCACTTAATCCTTTGTTTCTGACT
      733
823
CAAGATCCCCATGGGTTGTGTGTTTATTTCACTTGATGATACAATGAACACTTATAA
      853
943
AATGGCATGTCAGACACAGAACTTGAATGTGTCAGGTGACCCTGATGAAAACATAGCA
      973
1063
AAAGTAACTCATTTGTTAAAATTATCAATATCTAATATATGAATAAAGTGTAAG
      1093
```

FIG.5D.

```
643
ATCAAATAAGTATTTATAATAGCAACTTTTGTGTAATGAAAATGAATATCTATTAATATATGTA

763
AATTAGGCAAGGCTATGTGATTACAAGGCTTTATCTCAGGGGCCAACTAGGCAGCCAACCTAAG

883
GTGAAGTGATACTATCCAGTTACTGCCGGTTTGAAAATATGCCTGCAATCTCTGAGCCAGTGCTTT

1003
TCTCAGGAGATTTCATGCCTGGTGCTTCCAAATATTGTTGACAACTGTGACTGTACCCAAATGG

1123
TTCACAACTAAAAAAAAAAAAAAAAAAAACCCCCCCCCCCC
```

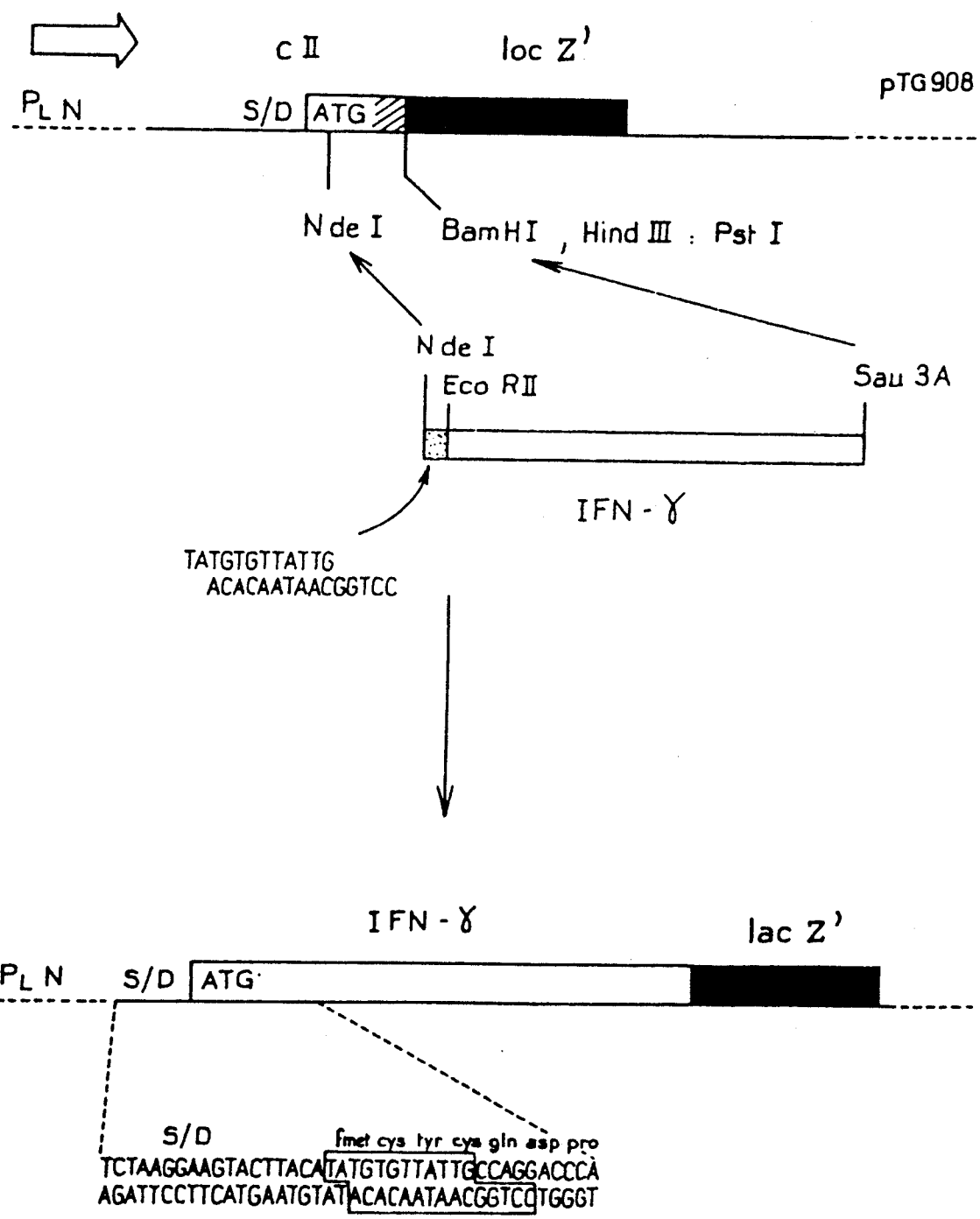
FIG_6

CONSTRUCTION OF PTG 941

PTG909

IFN

*MetCysTyrCysGlnAspProTyr*
TAAGGAAGTACTTA<u>CATATG</u>TGTTATTGCCAGGAC<u>CCATATG</u>....
              NdeI                        NdeI

NdeI
                      +
           TATGTGCTACTGTCAGGATCCC
            ACACGATGACAGTCCTAGGGAT

IFN

*MetCysTyrCysGlnAspProTyr*
PTG941   TAAGGAAGTACTTA<u>CATATG</u>TGCTACTGTCAGGATCCCTAT
                    NdeI                 BamHI

FIG_7

CONSTRUCTION OF PTG 951
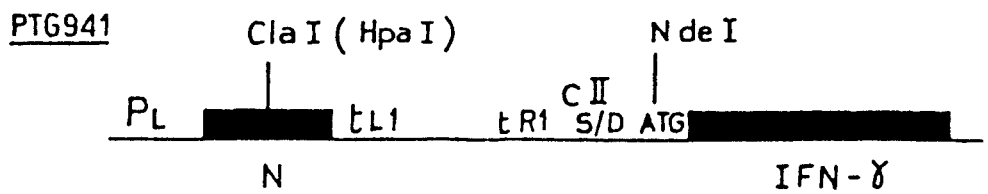
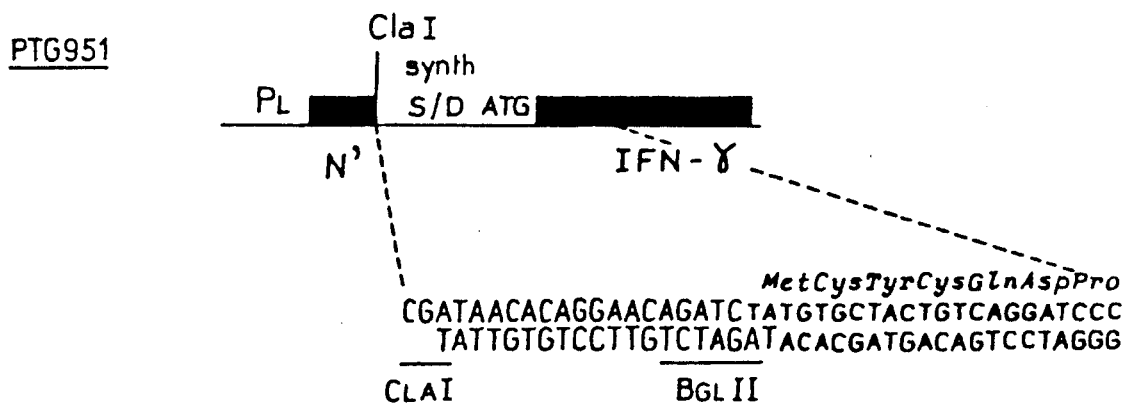
FIG_8

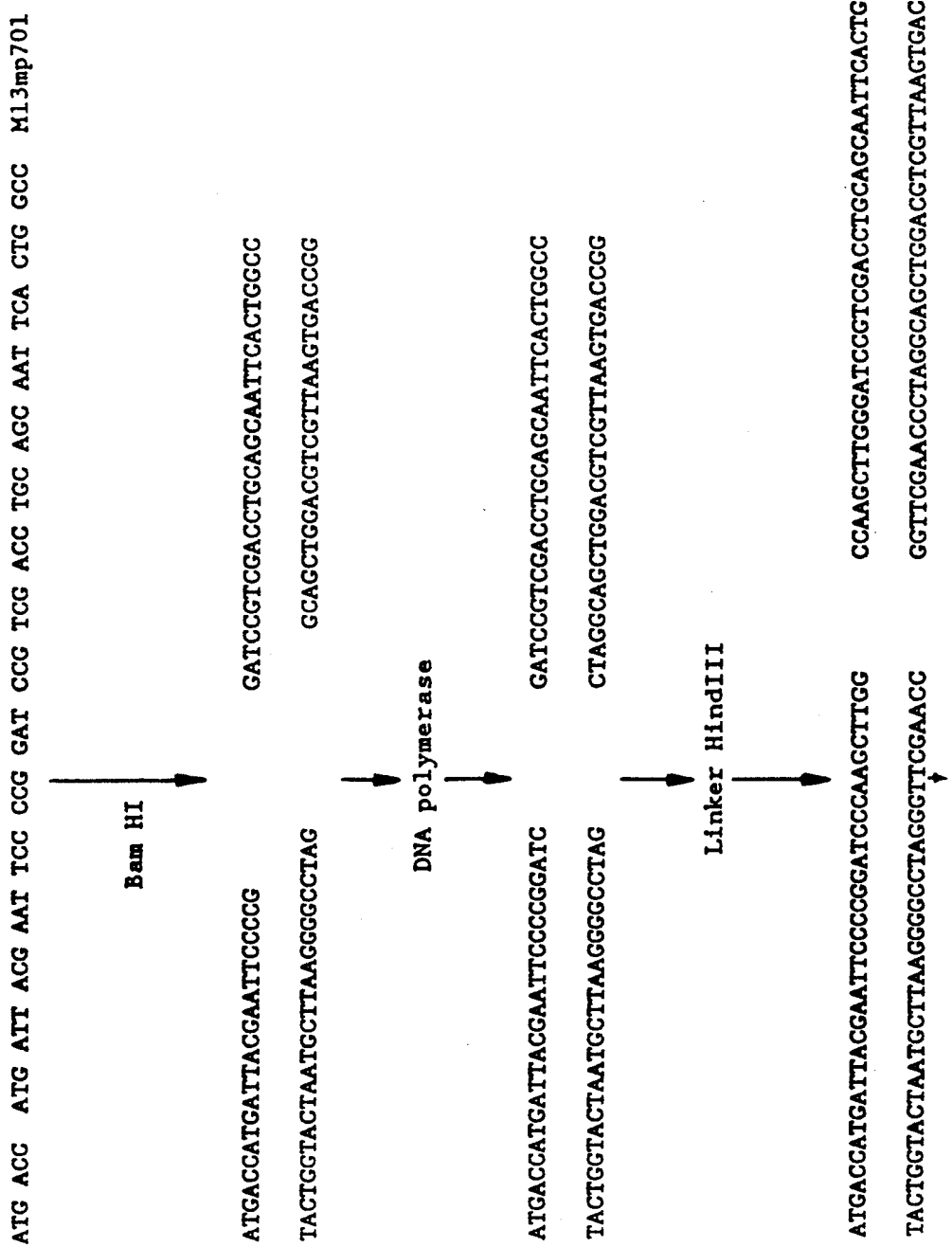

VECTOR FOR THE CLONING AND EXPRESSION OF γ-INTERFERON, TRANSFORMED BACTERIA AND PROCESS FOR THE PREPARATION OF γ-INTERFERON

This is a continuation of application Ser. No. 06/768,119, filed as PCT/FR84/000287, Dec. 5, 1984, now abandoned.

The present invention relates to a process for preparing human γ interferon.

γ interferon (hereinafter γ-IFN) is a glycoprotein endowed in vitro with a pronounced anti-tumor action. It forms the subject of many investigations at the pharmaceutical level. To provide for the growth of this product, it is appropriate to be able to prepare it in substantial amounts so as to bring down its price.

Carrying out genetic engineering techniques, it has been possible to describe the preparation of γ-IFN by bacterial fermentation, in particular in European Patent Application 0,077,670.

However, it does not appear that the yields obtained are particularly useful, and thus, in the patent mentioned above, the activity of the fermented medium is $2.5 \times 10^5$ γ-IFN U/L, which is poor from the standpoint of the yield.

The present invention has as its subject to increase the fermentation yield by a factor of 10,000 to 20,000, the amount of γ-IFN produced reaching 20% (of the total weight) of the bacterial proteins produced.

To achieve this, the present invention proposes new vectors.

This is a vector for the expression of the protein of γ interferon in bacteria, of the type containing the gene which codes for the protein of human γ interferon and the plasmid elements which provide for the expression of this gene, wherein the 5' end of the sequence coding for the protein is as follows:

5' $\overline{\text{ATG}}$ TGC TAC TGT CAG GAT CCC 3'

TAC ACG ATG ACA GTC CTA GGG

Met Cys Tyr Cys Gln Asp Pro

The beginning of the original, natural -IFN sequence is as follows (without the starting ATG codon):

ATG TGT TAC TGC CAG GAC CCA

Comparing this with the proposed sequence:

$\overline{\text{ATG}}$ TGC TAC TGT CAG GAT CCC four changes in nucleotides, which preserve the composition of the protein, are noted. In the Examples which follow, it will be shown that these changes enable the yield of γ-IFN to be multiplied by approximately 10,000, especially when vectors are used such as those to be described below.

The vectors according to the present invention contain, in addition to the gene coding for IFN with a 5' end, as described above:

the origin of replication of a bacterial plasmid;
a promoter, in particular all or part of a bacteriophage λ promoter: $P_L$, $P_R$ or $P'_R$,
a region coding for the initiation of the translation, incorporating the ATG of the 5' end of the γ-IFN gene.

The presence of an origin of replication for a plasmid is essential to enable the vector to replicate in the corresponding bacterial cells and, especially in the case of E. coli, the origin of replication of plasmid pBR322 will preferably be used. Plasmid pBR322 has, in effect, the advantage of yielding a high copy number, and thus of increasing the quantity of plasmids producing the desired protein.

Among bacteriophage λ promoters, the main leftward promoter designated λ $P_L$ will preferably be used. $P_L$ is a powerful promoter responsible for the early transcription of λ.

It is also possible to use other bacteriophage λ promoters, in particular the rightward promoter $P_R$, or the second rightward promoter $P'_R$.

Although it is possible to use very varied initiation sequences for the translation, the use of that of bacteriophage λ protein cII, hereinafter λIIrbs, is preferred.

As will be shown, it is also possible to use such synthetic sequences, especially all or part of the sequence:

ATAACACAGGAACAGATCTATG.

The vector in question preferably contains, in addition, a transcription antitermination function encoded, for example, by the N gene of λ designated λ N. In the presence of the N gene transcription product, transcription from $P_L$ continues beyond the majority of stop signals.

This avoids the problems caused by a premature stopping of transcription, which can arise when the cloned foreign genes possess such stop signals. Furthermore, it has been shown that expression from $P_L$ is improved in a N+ environment.

In order to avoid the problems of toxicity and instability of the host-vector system in cases of continuous production of large amounts of a foreign protein, it is necessary to provide for control of the activity of the promoter by uniting therewith all or part of an inducible, especially a heat-inducible, expression system.

Control by temperature of the synthesis of the foreign protein is preferably accomplished at the level of transcription by means of a temperature-sensitive repressor encoded in the host bacterium, for example cI857, which represses the activity of $P_L$ at 28° C. but is inactivated at 42° C. The repressor acts on the $O_L$ operator which is adjacent to the $P_L$ promoter. Although in the above case a portion of the heat-inducible expression system is an integral part of the host bacterium, it is possible to provide for this system to form part of the vector itself.

The vector in question can also contain a gene for resistance to an antibiotic, for example ampicillin in the case of pBR322, but other resistance genes can be used, resistance to tetracyclin (Tet^r) or chloramphenicol (Cm^r).

The incorporation of such a marker is necessary for the selection of the bacterial transformants carrying the plasmid according to the invention during the cloning experiments.

The incorporation of a resistance gene enables the stability of the plasmid to be increased by imposing a selection pressure during the fermentation and, furthermore, facilitates the isolation of the transformants.

For cloning, it is advantageous to have available a system for detecting the insertion of a foreign DNA in a plasmid.

By way of example, it is possible to provide, in the cloning region, for the N-terminal fragment of *E. Coli* β-galactosidase (LacZ') by fusing the fragment with the translation initiation region derived from cII, and this places the translation of the α fragment under the control of the cII sequences.

The α fragment is complemented by the expression of the C-terminal ω fragment encoded in the host, and this leads to β-galactosidase activity in the cells. This β-galactosidase activity produces blue colonies in the presence of a chromophoric substrate, 5-bromo-4-chloro-3-indolyl-β-D-galactosidase.

At 28° C., the $P_L$ promoter is inactivated, the α fragment is not synthesized and the colonies remain white. When the temperature is raised to 42° C., the $P_L$ promoter is activated, the α fragment is synthesized and the colonies turn blue.

The insertion of foreign DNA into the cloning sites situated in this detection system prevents the synthesis of β-galactosidase, and consequently leads to white colonies at both 28° C. and 42° C.

It is also possible to replace the lacZ' gene by other genes enabling detection to be achieved.

The present invention relates, in addition, to the bacteria, especially strains of *E. coli*, transformed by the vectors according to the invention by known techniques, some of which will be recalled in the Examples.

Finally, the invention relates to a process for preparing human γ-IFN, in which bacteria transformed as described above are cultured on a culture medium, and in which the γ-IFN formed is then recovered.

The culture media employed are known to those versed in the art, and will have to be adapted to suit each strain cultivated. Culturing will preferably be performed in the presence of the antibiotic to which the transformed strain has become resistant.

γ-IFN is separated after bursting the cells by known techniques such as affinity column separation or exclusion chromatography.

The present invention naturally incorporates other aspects, in particular certain plasmids which will be described in the Examples as well as the mutants and derivatives thereof and, generally, the processes for fermenting the transformed bacteria as well as the γ-IFN thereby obtained.

Other characteristics and advantages of the invention will be better understood on reading the Examples below and the attached drawings, in which:

BRIEF DESCRIPTION OF THE DRAWINGS

FIG. 2 shows the strategy for preparing phage M13tg910,

FIGS. 3A, 3B, 3C, and 3D show the structure of phage M13tg910,

FIG. 4 shows the strategy for preparing plasmid pTG908,

FIGS. 5A, 5B, 5C, and 5D show the complete sequence of the gene coding for γ-IFN isolated from the library, FIG. 6 shows the strategy for preparing pTG909, FIG. 7 shows the strategy for preparing pTG941, FIG. 8 shows the strategy for preparing pTG951.

FIGS. 9A and 9B show the construction scheme for plasmid M13mp701.

Figure 1:
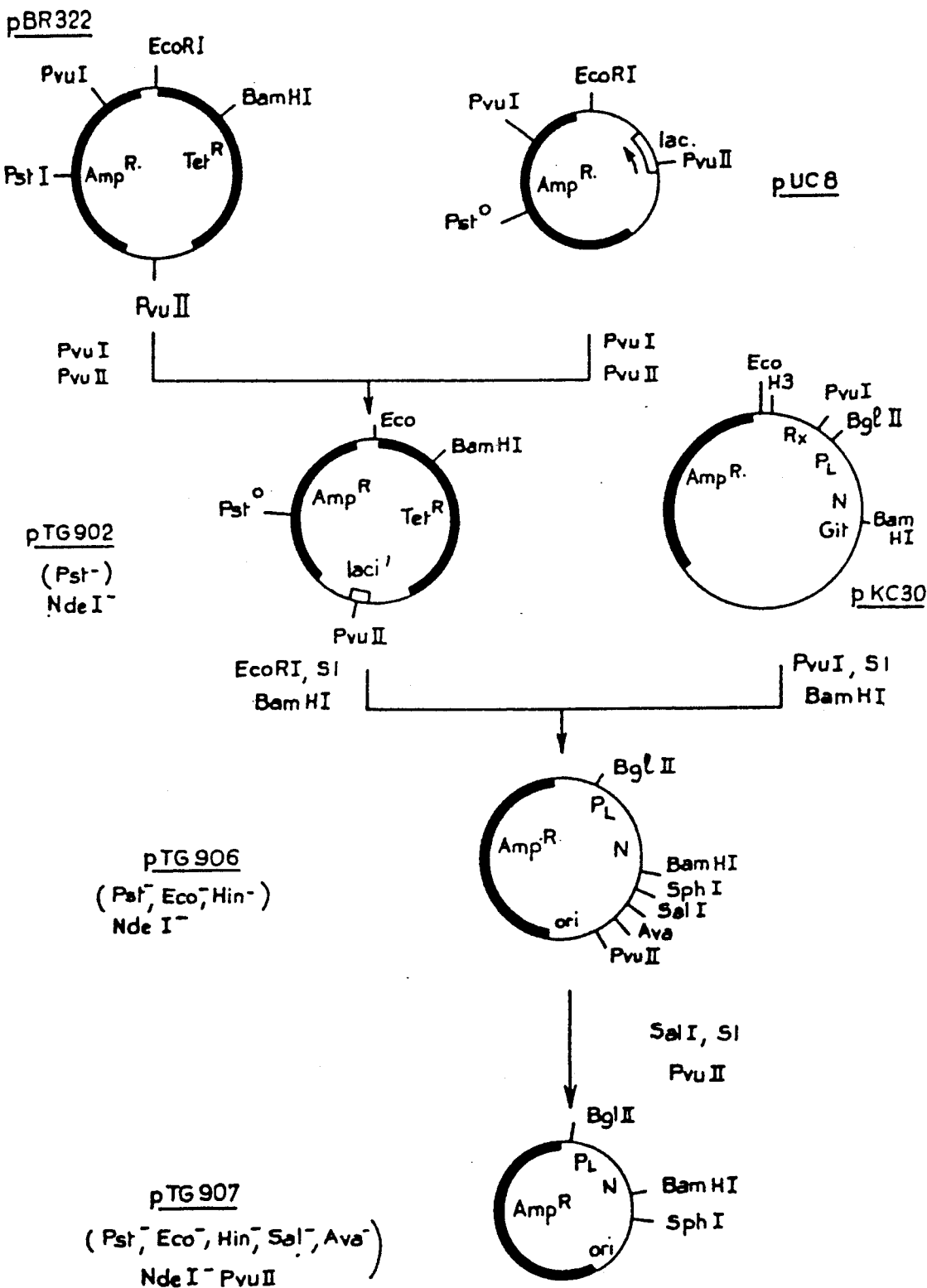
FIG. 1 shows the strategy for preparing plasmid pTG907.
Figure 3B:
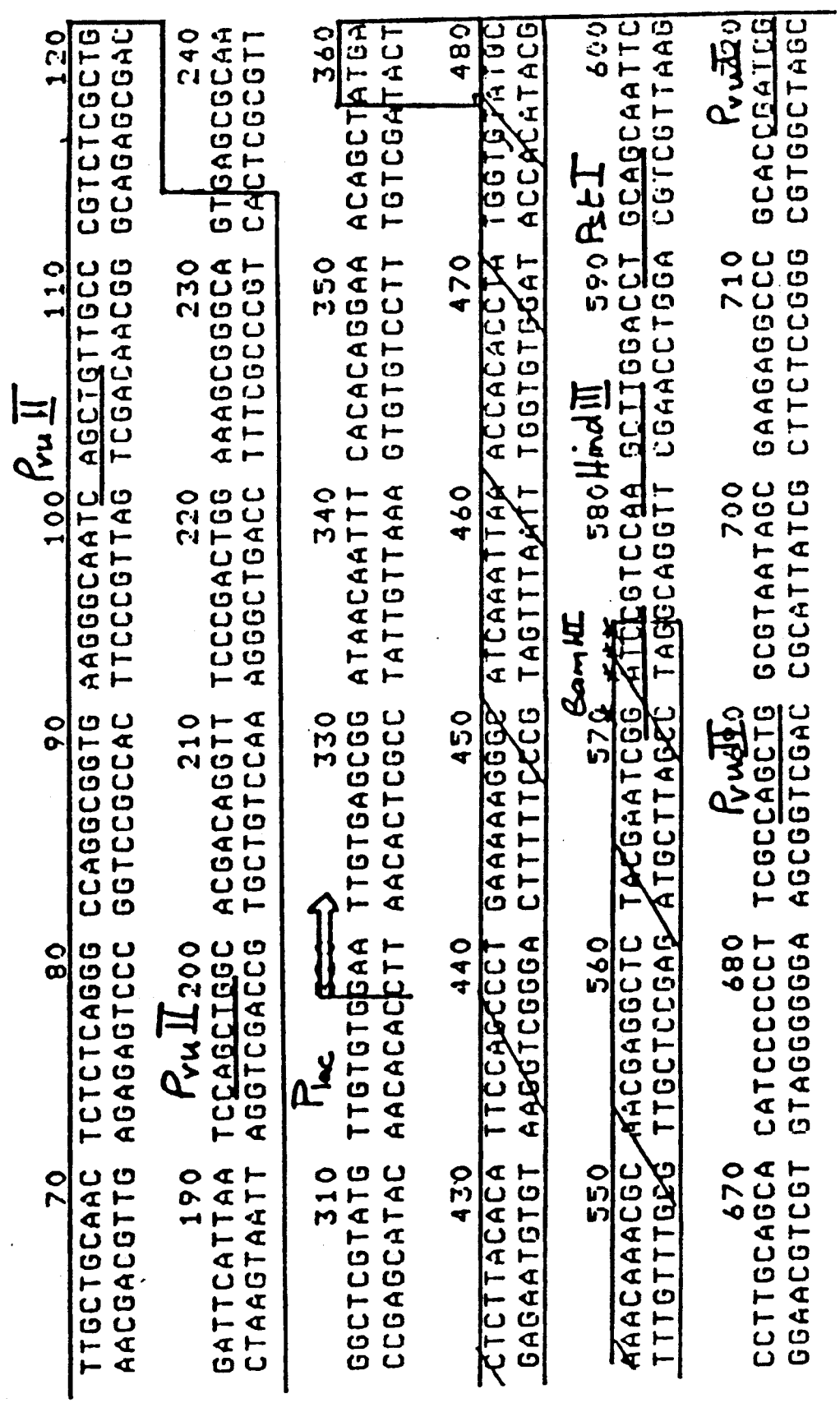

It is appropriate to note that the different nucleotide sequences appearing in the drawings must be considered to form an explicit part of the present description, and these sequences have not been reproduced in the body of the text in order not to encumber it unnecessarily.

1) GENERAL METHODS a) Bacterial Strains

The bacterial strains used in the context of the present invention are as follows:

TGE900, which is an *E. coli* strain having the following characteristics: su$^-$F$^{31}$ his ilv bio (λcI857-ΔBamΔHI)

N6437, an *E. coli* strain having the following characteristics: F$^-$his ilv gal$^+$ Δ8proc$^+$: tn10 lacΔm15 (λcI857ΔBamΔHI).

Jm103, which is an *E. coli* strain having the following characteristics: Δ (lac-pro) sup$^E$ thi endA sbcB15 sttA rK$^-$ /F$^1$ traD36 proAB$^+$ laci$^a$ lacZ m15.

The strains mentioned above were used because they were available, but it is clearly understood that it is possible to use other strains provided that they have certain essential characteristics which are recalled in the course of the detailed description.

b) Preparation of the DNA

Plasmid or phage M13 DNA mini-preparations are performed as described by Ish-Horowitz (Reference 1), with the single difference that the DNA is precipitated a second time with ethanol before being used.

The maxi-preparations are performed as described in the above publication, with an additional purification using a CsCl/ethidium bromide density gradient.

c) Cloning Techniques

Treatment of the DNA with restriction enzymes is performed, except where otherwise stated, using the conditions indicated by the manufacturer (New England Biolabs, Bethesda Research Laboratories and Boehringer Mannheim).

When necessary, the phosphates at the 5' ends are removed using either a bacterial alkaline phosphatase or a calf intestinal phosphatase, for 30 minutes at 37° C. in the restriction enzyme buffer.

The repair of the cohesive ends using the Klenow polymerase (Boehringer Mannheim) is performed at 25° C. for 15 minutes in a mixture of 50 mM Tris HCl, pH 7.8, 5 mM MgCl2, 10 mM β-mercaptoethanol, 0.4 mM of dNTps with the enzyme and 10 to 200 μg/ml of DNA.

S$_1$ nuclease (Miles) is used at 2 u/μg of DNA at 25° C. for 30 minutes in a 0.3M NaCl, 0.03M NaOAc, pH 4.8, 0.003M ZnCl$_2$ medium.

Bal31 is used according to the method of Panayotatos et al. (Reference 2). The ligations are performed at 15° C. (except where otherwise stated) for 4 to 24 hours using T$_4$ DNA ligase (Boehringer Mannheim) with 100 mM NaCl, 66 mM Tris HCl, pH 7.5, 10 mM MgCl$_2$, 0.5 mM spermidine, 0.2 mM EDTA, 2 mM DTT, 1 mM ATP, 0.1 mg/ml of BSA and 5 to 50 μg/ml of DNA.

For the ligation of cohesive ends, approximately 30 units/ml of ligase are used. For the ligation of blunt ends, approximately 100 units/ml of ligase are used.

Between the different enzyme reactions, DNA samples are extracted with a phenol/chloroform mixture and then precipitated with ethanol. Where necessary, *E. coli* or yeast tRNA is used as an entraining agent. The molecular adaptors (Collaborative Research, Bethesda Research Laboratories, New England Biolabs) are prehybridized and used in a 10- to 50-fold molar excess for the blunt ends DNAs using the buffer conditions described above with 100 units/ml of $T_4$ ligase at 4° C. for 15 hours. When non-phosphorylated adaptors are used, the adaptors which have not reacted are removed directly after ligation by precipitation with spermine tetrahydrochloride (Hoopes et al.—Reference 3).

When phosphorylated adaptors are used, the ligation mixture is first extracted with a phenol/chloroform mixture and then precipitated with ethanol before specific cleavage with the appropriate restriction enzymes, followed by precipitation with spermine tetrahydrochloride.

The competent bacterial cells are prepared and then transformed with the plasmids or transfected with M13 DNA according to the methods described by Dagert and Ehrlich (Reference 4).

EXAMPLE 1

Preparation of pTG908 first involves the preparation of a plasmid containing:
the origin of replication of pBR322,
the gene for resistance to ampicillin of this same plasmid ($amp^R$),
the $P_L$ promoter and the λ N gene.

1) Elimination of the PstI Site in pBR322

The basic plasmid used is plasmid pBR322; however, the latter has the disadvantage of having a PstI restriction site inside the $amp^R$ gene, since a site of the same kind will be used subsequently in the cloning region as a single restriction site. It is then appropriate to cause this PstI restriction site to disappear, using a mutant of plasmid pBR322, plasmid pUC8, in which the gene for resistance to ampicillin does not have a PstI restriction site (this site has been removed by mutation in vitro). pBR322 is marketed, in particular, by Bethesda Research Laboratories and pUC8 is described in the article in Reference 5.

To achieve this, the 1,669 bp PvuI-PvuII fragment of pBR322 is exchanged with the similar PvuI-PvuII fragment of plasmid pUC8. To carry out this exchange, plasmids pBR322 and pUC8 are treated successively with PvuI and PvuII, and then circularized by the action of a ligase.

Plasmid pTG902, which no longer has a PstI restriction site and which has also lost the NdeI restriction site present originally on pBR322 (not shown in FIG. 1), is thereby obtained. Furthermore, plasmid pTG902 carries a 50 bp fragment corresponding to the laci' sequence in which the PvuII site is present.

2) Insertion of the $P_L$ Promoter and the λ N Gene and Preparation of Plasmid pTG907

The $P_L$ promoter and the λ N gene are isolated from plasmid pKC30 and inserted in pTG902, the segment removed also containing the $O_L$ operator on which the temperature-sensitive represser cI850 will act, as will be described in the tests. Furthermore, the method enables the EcoRI and HindIII sites to be eliminated while retaining a single BamHI site downstream of the N gene so that λcIIrbs can then be inserted. Plasmid pKC30 is described in Reference 6.

pTG902 is cut at its single EcoRI restriction site and protruding 5' ends are removed by treatment with $S_1$ nuclease. After digestion with BamHI, the most substantial fragment is purified on gel.

The fragment carrying the $P_L$ promoter and the λN gene is prepared in the same manner from pKC30 by successively treating the plasmid with PvuI, $S_1$ nuclease and BamHI. After purification on the gel, the fragments are subjected to the action of the ligase, which leads to the EcoRI/PvuI fusion and reconstitution of the BamHI site.

The ligation mixture is used for transforming competent TGE900 host cells at 30° C. This strain contains the deleted prophage λ, λ cI857ΔBamΔHI, which provides the temperature-sensitive λ repressor, cI857, which is required for blocking the transcription from $P_L$.

This is important, since $P_L$ activity in an N+ medium is lethal on account of the antitermination function of N.

After analysis with restriction enzymes, the clones contain plasmids having the correct structure and are then tested for their lack of viability at 42° C.

One of the plasmids obtained, pTG906, is treated so as to remove the PvuII-SalI segment so as to eliminate the restriction sites included on this segment, and in order to cause the two end restriction sites to disappear also. To achieve this, pTG906 is treated successively with SalI, $S_1$ nuclease, PvuII and the ligase.

Plasmid pTG907, which contains the combination of elements mentioned at the beginning of this stage, and which, in addition, is Pst⁻ Eco⁻ Hind⁻ Sal⁻ Ava⁻ Nde⁻ PvuII⁻, is thereby obtained. The synthesis of this plasmid is shown in FIG. 1.

3) Cloning of the λ cIIrbs Region

The second important phase of the synthesis consists in inserting the λcIIrbs region in the form of an AvaI-TaqI fragment in the beginning of the lacZ' gene (α fragment of β-galactosidase) which has been cloned in the phage M13 called M13tg110. This strategy enables a simple functional test for rbs to be performed, namely, the production of the lacZ' protein, and consequently blue plaques to be obtained in the presence of IPTG and Xgal; this also enables rapid sequencing of the construction using the so-called dideoxy method.

In the course of the experiments, different derivatives of phage M13 will be mentioned. Phage M13tg110 has been mentioned above, and in the remainder of the description other phages of the same type, the construction of which will be recalled below, will be used.

The construction of these vectors is indicated in Table I below, in which there are shown the references for the starting phage, the nature of the restriction enzyme with which it has been cut, the particular treatment undergone by the fragments thereby obtained, and the nature of the insert which has been bound in the sites thereby revealed.

Phage M13mp7 is marketed in particular by Bethesda Research Laboratories.

M13mp701 is obtained from M13mp7 by replacement of the PstI-EcoRI fragment to the right (CTG CAG . . . GAA TTC) by the sequence: CTG CAG CAA TTC.

Figure 9B:
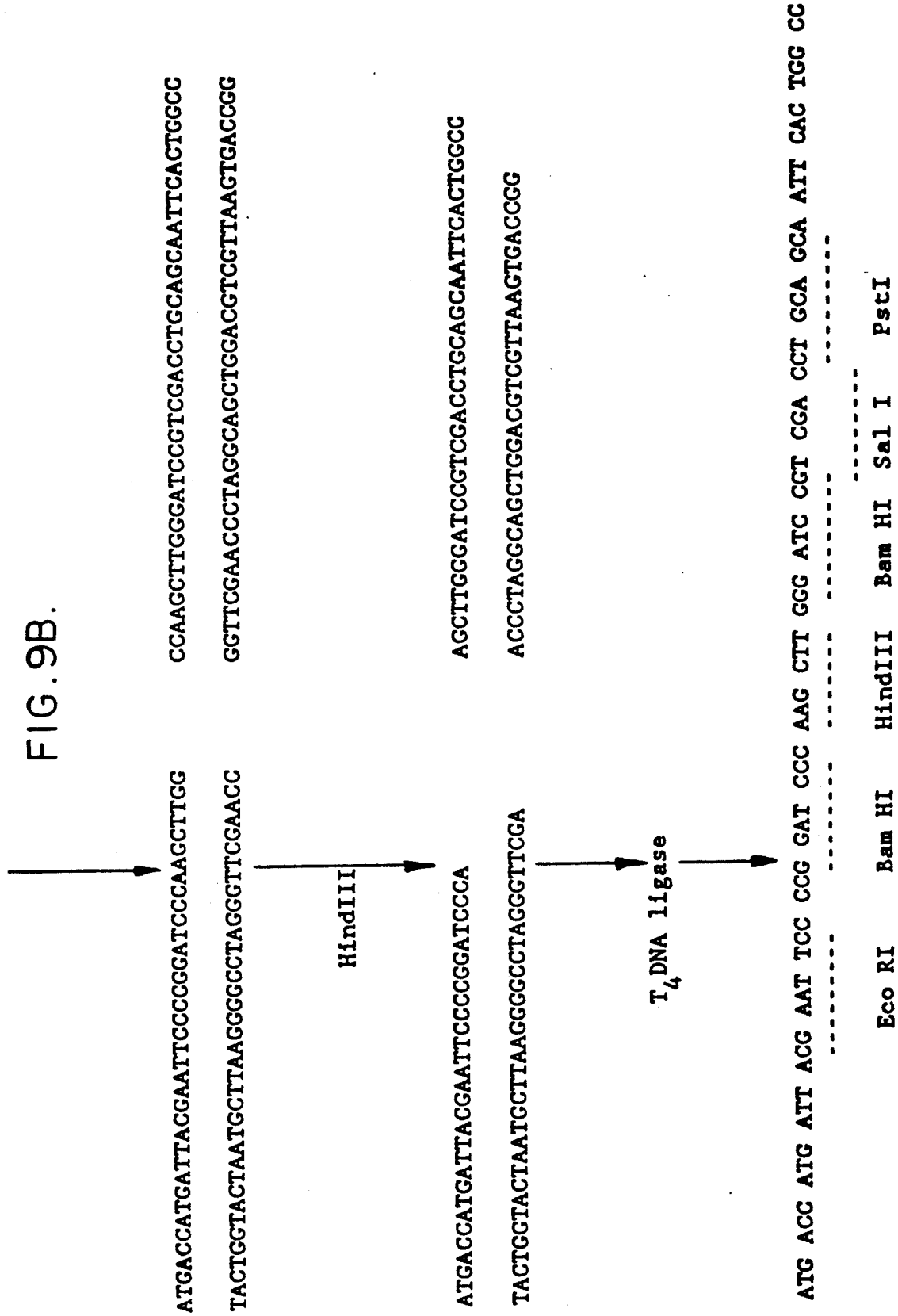

The principle of the construction is described in the scheme shown in FIGS. 9A and 9B.

TABLE I

| Name | Parent phage | Site of cleavage | Treatment | Insert | Hind III phase | BamHI phase | PstI phase | Complementation of Lacα +/− |
|---|---|---|---|---|---|---|---|---|
| M13mp701 | M13mp7 | Construction | D. R. Bentley | | 0 | I | I | + |
| M13tg102 | M13mp701 | AccI | DNA polymerase | HindIII (a) sequence | I | I | I | + |
| M13tg110 | M13mp701 | AccI | S₁ nuclease | HindIII (a) sequence | III | I | II | − |
| M13tg115 | M13tg110 | EcoRI | S₁ nuclease | BglII (b) sequence | II | III | I | + |

(a) Phosphorylated adaptor of HindIII sequence CCAAGCTTGG
(b) Non-phosphorylated adaptor of BglII sequence CAGATCTG The procedures for using the enzymes (restriction, DNA polymerase, T₄DNA ligase) are those given in the suppliers' leaflets. The HindIII linker is a synthetic oligonucleotide of sequence

(Collaborative Research Inc., Waltham, Mass. 02154, USA).

The cIIrbs region is isolated from a plasmid pOG11 (Ref 7) which contains a λHaeIII-Sau3A fragment which extends from the middle of the cro gene to the middle of the region coding for cII (cro and cII being involved, in particular, in the regulation of lysogeny of bacteriophage λ).

The 186 bp AvaI-TaqI fragment containing the cIIrbs region is removed from pOG11 and treated with the Klenow polymerase. In addition, phage M13tg110 is treated with BamHI and then with the Klenow polymerase followed by treatment with calf intestinal phosphatase. The fragments obtained are subjected to the action of T₄ ligase.

Examination of the sequences of the pOG11 fragment containing the cIIrbs region and of phage M13tg110 enables to be predicted that the insertion of the fragment carrying cIIrbs in the BamHI site of M13tg110 must lead to the production of blue plaques after fermentation of the transfected bacteria, since the lacZ' gene is in phase for translation from AUG of the cII gene, while the plaques corresponding to the parent M13tg110 strain are white.

The blue plaques are withdrawn and the colonies are then selected by restriction enzyme analysis of the mini-preparations, and it is then checked by sequencing that the construction obtained is correct.

A resultant clone M13tg910 is thereby obtained, the overall structure of which is shown at the bottom of FIG. 2 and the detailed structure of which is shown in FIGS. 3A, 3B, 3C, and 3D.

It is observed that the insertion of the cIIrbs fragment reconstructs the BamHI and AvaI sites upstream and the BamHI site downstream.

Translation from AUG of cII leads to the fusion of the 13 terminal amino acids of cII to the 8 amino acids of the NH₂-terminus of the lacZ' protein.

4) Insertion of the λcIIrbs Fragment into Plasmid pTG907

The third stage of this synthesis consists in transferring the cIIrbs/lacZ' fragment of phage M13tg910 to the previously prepared plasmid vector pTG907.

To achieve this, it is first appropriate to remove the EcoRI, BamHI and AvaI sites upstream of cIIrbs and then insert a BglII site.

Under these conditions, cIIrbs can be withdrawn in the form of a BglII-BglII fragment and placed in the BamHI site upstream of the $P_L$ promoter and the λN gene of pTG907.

Phage M13tg910 is digested with EcoRI, then treated with Bal31 and then subsequently with the Klenow polymerase. The fragments obtained are then subjected to the action of the ligase in the presence of non-phosphorylated BglII adaptors. The ligation mixture obtained is used for transforming competent JM103 cells. The blue areas are then selected. These clones are then analyzed in order to check that they contain the BglII site and that they no longer have an EcoRI or BamHI site upstream. Clones such as M13tg912, the structure of which is shown in FIG. 4, are thereby obtained.

The treatment with Bal31 has produced a 101 bp deletion removing the EcoRI, BamHI and AvaI sites; and also the ATG lac and Shine/Dalgarno lac sequences. The BglII site introduced is situated approximately 100 bp upstream of the ATG of cII and 10 bp downstream of $P_{lac}$.

The BamHI-SphI fragment of pTG907, the BglII-HgaI fragment carrying cIIrbs and lacZ' and the phosphorylated adaptor were prehybridized in a mole ratio of 1:2:1, and then treated with T₄ ligase. Aliquots are used for transforming competent cells of strain 6150 at 30° C.

The cells of interest are identified by selecting the transformants with a ³²P-labeled cIIrbs/lacZ' fragment, and the construction obtained is confirmed by restriction enzyme study.

In order to obtain an initial indication showing that the different elements of the expression system behave as desired, the plasmid obtained, pTG908, is transformed into a host strain N6437 which possesses both c1857 and the ω fragment of β-galactosidase complementing the α fragment which is encoded by the plasmid.

The transformants obtained, placed in a dish containing IPTG+Xgal are white at 28° C. and then turn blue approximately 30 minutes later when they are transferred to 42° C.

EXAMPLE 2

Selection of the Clone of cDNA of Human γ-IFN

By known methods, a library of cDNA is produced from the mRNA of lymphocytes induced by mitogenic agents.

A clone containing the sequence coding for complete γ-IFN (FIGS. 5A, 5B, 5C, and 5D) is then selected, this clone being named pTG11.

γ-IFN is synthesized in the form of a prepeptide from which the signal sequence of 20 amino acids is split off to give the polypeptide, which begins with the sequence cys-tyr-cys and embraces amino acids 21 to 166.

Analysis of the nucleotide sequence for the restriction sites reveals an EcoRII site 8 bp downstream of the starting point of the protein and an Sau3A site 285 bp downstream of the stop codon, and this enables virtually the entire sequence coding for the protein to be isolated on an EcoRII-Sau3A fragment.

EXAMPLE 3

Construction of pTG909, a Plasmid Weakly Yielding Human γ-IFN

FIG. 6 shows schematically the preparation of pTG909.

A synthetic adaptor molecule is first used which enables:

a) joining to be accomplished between the EcoRII NdeI ends,
b) the 8 bp, missing with respect to the sequence coding for γ-IFN, to be introduced, and
c) the ATG starting codon of cIIrbs to be reconstituted, so that the sequence coding for the γ-IFN protein is translated without fused amino acids with the exception of the F-met initiator.

This adaptor is chemically synthesized and its constitution is shown in FIG. 2.

pTG11 is digested with EcoRII and Sau3A, and pTG908 with NdeI and BamHI.

The appropriate fragments are purified on gel, mixed with an equimolar amount of the adaptor, prehybridized and ligated. The mixture is used for transforming competent TGE900 cells and the transformants are selected by hybridizing a nick-translated, $^{32}$P-labeled PstI insert of pTG11 with the transformants.

13 clones are selected and monitored by mapping, and one of them, pTG909, is checked by sequencing.

Culturing of the clone of TG900 transformed by TG909 is performed on an LB medium with 50 μg/ml of ampicillin to an optical density $OD_{660}$ of 0.3 (~$10^8$ cells/ml) and induced for 1 hour at 42° C. The extracts are prepared for testing their γ-IFN activity according to known methods.

The results show a γ-IFN activity of $10^5$ units/l of culture. The molecular weight of the protein, approximately 17,000 daltons, is in good agreement with what is known for γ-IFN.

However, this activity corresponds to approximately 0.001% of the total protein content of the cell.

This result led to a reexamination of the fine structure of the bases in the neighborhood of the starting codon and to the proposal that conservative point mutations be effected to enable the γ-IFN yield to be improved.

EXAMPLE 4

Construction of Vector pTG941 pTG909 contains 2 NdeI sites, one at the starting codon of γ-IFN and the other 22 bp later in the γ-IFN sequence (see FIG. 7).

The region between these sites, which is the region coding for the first 7 amino acids of γ-IFN, was removed by treatment with NdeI and replaced by a synthetic oligonucleotide which is shown in FIG. 7.

This reaction destroys the NdeI site downstream and reconstitutes the NdeI site upstream, while introducing a BamHI site which is unique.

This change of base is conservative, that is to say that the amino acid sequence is not adversely affected.

The extracts obtained under the same conditions as above, starting from strain transformed by plasmid pTG941, contain $2 \times 10^9$ U/l of γ-IFN.

This result is 10,000 times better than the results obtained with pTG909, and corresponds to 10% of the total weight of the cellular proteins produced.

EXAMPLE 5

Construction of pTG951

Plasmid pTG951, in *E. coli* was deposited on July 25, 1990, at the Collection Nationale de Cultures de Microorganismes of Institut Pasteur, 25, Rue du Docteur Roux, 75724 Paris Cedex 15, and will be maintained in accordance with the Budapest Convention. The deposit number is I-983. Deposit is for the purpose of enabling disclosure only and is not intended to limit the concept of the present invention to the particular materials deposited.

FIG. 8 shows schematically the construction of pTG951, which is a derivative of pTG941 in which a fragment containing the cIIrbs has been replaced by a synthetic sequence based on the sequence of the translation initiation region of the *E. coli lac* operon, designated *E. coli lac* operon rbs. This synthetic oligonucleotide was inserted between the single NdeI site of the starting codon of the sequence coding for γ-IFN and the ClaI site which was inserted at the HgaI site in the N gene. As a result of this, on treatment with NdeI and ClaI, plasmid pTG951 now contains only a truncated N gene (a stop codon in phase with the translation of the N gene is placed immediately upstream of the new rbs site) and is devoid of the transcription terminators tL1 and tR1 present in pTG909 and pTG941.

The bacterial extracts obtained using bacteria transformed by pTG951 lead to the production of $5 \times 10^9$ γ-IFN U/l of culture, which corresponds to 25% of the total weight of the cellular proteins produced.

The synthetic rbs site of pTG951 contains a single BglII site immediately before the starting codon, and it is hence possible to make derivatives of pTG951 by cleavage with BglII followed by various manipulations using either DNA polymerase I or S1 nuclease. These derivatives have variations in the distance and the sequences between the Shine/Dalgarno sequence and the ATG. However, none of the plasmids thereby prepared has superior activity to pTG951 itself.

The main results are recorded in the Table below:

TABLE

| NAME | PROMOTER | RBS | RBS SEQUENCE AND JUNCTION WITH THE IFN SEQUENCE | U IFN/l | % PROTEIN |
|---|---|---|---|---|---|
| pTG909 | PL | cII |                                 fmet  cys  tyr  cys  gln  asp  pro  tyr<br>TAAGGAAGTACTTACATATG TGT TAT TGC CAG GAC CCA TAT | $10^5$ U | NOT DETECTED |

TABLE-continued

| NAME | PRO-MOTER | RBS | RBS SEQUENCE AND JUNCTION WITH THE IFN SEQUENCE | U IFN/1 | % PROTEIN |
|---|---|---|---|---|---|
| pTG941 | PL | cII | TAAGGAAGTACTTACATATG TGC TAC TGT CAG GAT CCC TAT<br>                         fmet  cys  tyr  cys  gln  asp  pro  tyr | $2 \times 10^9$ U | >10% |
| pTG951 | PL | SYNTH (lac) | CACAGGAACAGAGATCTATG TGC TAC TGT CAG GAT CCC TAT<br>                  BglII    fmet  cys  tyr  cys  gln  asp  pro  tyr | $5 \times 10^9$ U | >10% |

REFERENCES

1. Ish-Horowitz D. and Burke J. F., Nucl. Acids Res. 9, 2989–2998 (1981).
2. Panayotatos N. and Trong K., Nucl. Acids Res. 9, 5679–5688 (1981).
3. Hoopes B. C. and McClure R. R., Nucl. Acids Res. 9, 5493–5504 (1981).
4. Dagert M. and Ehrlich S. D., Gene, 23–28 (1979).
5. Vieira J. and Messing J., Gene 19, 259–268.
6. Shimatake H. and Rosenberg M., Nature, 292, 128–132, (1981).
7. Oppenheimer A. B., Gottesman S. and Gottesman M., J. Mol. Biol., 158, 327–346 (1982).

We claim:

1. Vector for the expression of the protein of human γ interferon in bacteria, of the type containing the gene which codes for the protein of human γ interferon and the plasmid elements which provide for the expression of this gene, wherein the 5' end of the sequence coding for the protein is as follows:

5' ATG TGC TAC TGT CAG GAT CCC 3'

TAC ACG ATG ACA GTC CTA GGG

Met Cys Tyr Cys Gln Asp Pro.

2. Cloning vector as claimed in claim 1, which contains in addition,
   a) the origin of replication of a bacterial plasmid,
   b) a promoter,
   c) a translation initiation region containing the ATG codon of the sequence coding for γ-IFN.
3. Vector as claimed in claim 2, which contains:
   a) the origin of replication of a bacterial plasmid,
   b) a bacteriophage promoter, $P_L$, $P_R$ or $P'_{R'}$,
   c) a translation initiation region chosen from λcIIrbs or a synthetic sequence placed under the control of the bacteriophage λ promoter.
4. Vector as claimed in claim 2, in which the region consists of the sequence:

ATAACACAGGAACAGATCTATG.

5. Vector as claimed in claim 2, in which the translation initiation region is λcIIrbs.
6. Vector as claimed in claim 1 which further includes as a transcription antitermination sequence, the N-gene of bacteriophage λ.
7. Vector as claimed in claim 1, which contains the origin of replication of pBR322.
8. Vector as claimed in claim 1, which contains a gene coding for resistance to an antibiotic.
9. Vector as claimed in claim 8, which contains a gene for resistance to ampicillin.
10. Bacteria transformed by a vector as claimed in claim 1.
11. Bacteria as claimed in claim 10, which are E. coli.
12. Process for preparing human γ interferon, wherein a bacterium as claimed in claim 10 is cultured on a culture medium, and wherein the human γ-IFN obtained after culturing is isolated.
13. Vector as claimed in claim 1 wherein an element providing for expression is the $P_L$ promoter.
14. Plasmid vector pTG951.

* * * * *